US010736663B2

(12) United States Patent
Tang et al.

(10) Patent No.: US 10,736,663 B2
(45) Date of Patent: Aug. 11, 2020

(54) MODIFIED VERESS NEEDLE FOR TENSION PNEUMOTHORAX DECOMPRESSION

(71) Applicant: The Arizona Board of Regents on Behalf of the University of Arizona, Tucson, AZ (US)

(72) Inventors: Andrew Tang, Tucson, AZ (US); Peter Rhee, Tucson, AZ (US)

(73) Assignee: The Arizona Board of Regents on Behalf of The University of Arizona, Tucson, AZ (US)

( * ) Notice: Subject to any disclaimer, the term of this patent is extended or adjusted under 35 U.S.C. 154(b) by 746 days.

(21) Appl. No.: 14/771,750

(22) PCT Filed: Mar. 3, 2014

(86) PCT No.: PCT/US2014/020027
§ 371 (c)(1),
(2) Date: Aug. 31, 2015

(87) PCT Pub. No.: WO2014/134624
PCT Pub. Date: Sep. 4, 2014

(65) Prior Publication Data
US 2016/0022312 A1    Jan. 28, 2016

Related U.S. Application Data

(60) Provisional application No. 61/771,442, filed on Mar. 1, 2013.

(51) Int. Cl.
*A61B 17/34* (2006.01)
*A61M 5/32* (2006.01)
(Continued)

(52) U.S. Cl.
CPC ...... *A61B 17/3474* (2013.01); *A61B 17/3496* (2013.01); *A61M 5/3297* (2013.01); *A61B 2090/0811* (2016.02); *A61M 1/04* (2013.01)

(58) Field of Classification Search
CPC ............ A61B 17/3474; A61B 17/3496; A61B 2017/00455; A61B 90/03; A61B 1/00089;
(Continued)

(56) References Cited

U.S. PATENT DOCUMENTS 2,623,521 A * 12/1952 Shaw ...................... A61M 5/32
600/566
3,090,384 A * 5/1963 Baldwin ............. A61M 5/3286
604/272
(Continued)

FOREIGN PATENT DOCUMENTS

CN     203425005    2/2014
WO     WO 83/000429  2/1983
WO     WO 09/068661  6/2009

OTHER PUBLICATIONS

International Search Report dated Jun. 10, 2014, by the ISA/FIPS, for International Patent Application No. PCT/US2014/020027, 2 pp.
(Continued)

*Primary Examiner* — Scott J Medway
(74) *Attorney, Agent, or Firm* — Klarquist Sparkman, LLP

(57) ABSTRACT

Disclosed are devices and methods for treating tension pneumothorax. A needle assembly may include an outer cannula defining a lumen and having a distal end portion with a sharp bevel, and an inner cannula slidably-disposed through the lumen of the outer cannula. The inner cannula moves between an extended and retracted position and includes a blunt distal end portion configured to extend beyond the sharp bevel of the outer cannula when the inner cannula is in the extended position. The blunt distal end portion can retract within the lumen of the outer cannula when the inner cannula is in the retracted position, thereby exposing the sharp bevel. The needle assembly further includes a bias disposed inside the housing and coupled to
(Continued)

the inner cannula. A proximal end portion of the inner cannula is configured to extend through the housing when the inner cannula is in the retracted position.

22 Claims, 8 Drawing Sheets

(51) Int. Cl.
*A61M 1/04* (2006.01)
*A61B 90/00* (2016.01)

(58) Field of Classification Search
CPC ... A61B 1/015; A61B 17/3415; A61B 1/0008; A61B 5/150389; A61B 10/025; A61B 10/0258; A61B 10/0283; A61B 2010/0208; A61B 10/0233; A61B 17/1671; A61B 17/3401; A61B 17/3468; A61B 17/3472; A61M 2039/062; A61M 2039/0633; A61M 25/06; A61M 25/0631
See application file for complete search history.

(56) References Cited

U.S. PATENT DOCUMENTS

| | | | | |
|---|---|---|---|---|
| 4,403,617 | A * | 9/1983 | Tretinyak | A61B 10/025 600/567 |
| 4,447,235 | A | 5/1984 | Clarke | |
| 4,702,260 | A * | 10/1987 | Wang | A61B 10/0283 600/564 |
| 4,813,941 | A | 3/1989 | Shea | |
| 4,869,717 | A * | 9/1989 | Adair | A61B 17/3496 604/506 |
| 5,030,207 | A * | 7/1991 | Mersch | A61M 25/0693 604/168.01 |
| 5,098,388 | A * | 3/1992 | Kulkashi | A61B 17/3496 604/158 |
| 5,104,381 | A * | 4/1992 | Gresl | A61B 1/00135 604/158 |
| 5,217,438 | A | 6/1993 | Davis et al. | |
| 5,300,046 | A | 4/1994 | Scarfone et al. | |
| 5,334,159 | A | 8/1994 | Turkel | |
| 5,343,853 | A * | 9/1994 | Komi | A61B 1/00098 600/107 |
| 5,354,288 | A * | 10/1994 | Cosgrove | A61M 25/0068 604/264 |
| 5,374,252 | A * | 12/1994 | Banks | A61B 17/3496 600/567 |
| 5,380,290 | A * | 1/1995 | Makower | A61M 25/06 604/160 |
| 5,560,373 | A * | 10/1996 | De Santis | A61B 10/0283 600/566 |
| 5,685,852 | A * | 11/1997 | Turkel | A61B 17/3401 604/159 |
| 5,725,506 | A * | 3/1998 | Freeman | A61B 17/3415 600/579 |
| 5,971,960 | A | 10/1999 | Flom et al. | |
| 5,997,486 | A * | 12/1999 | Burek | A61B 10/0045 600/573 |
| 6,077,179 | A * | 6/2000 | Liechty, II | F42B 6/08 473/582 |
| 6,447,483 | B1 * | 9/2002 | Steube | A61B 17/3415 604/158 |
| 6,702,790 | B1 * | 3/2004 | Ross | A61M 5/3286 604/239 |
| 6,742,519 | B2 | 6/2004 | Turnbull | |
| 6,770,070 | B1 * | 8/2004 | Balbierz | A61B 10/04 600/566 |
| 6,869,430 | B2 * | 3/2005 | Balbierz | A61B 18/1206 606/41 |
| 7,229,433 | B2 | 6/2007 | Mullen | |
| 7,591,807 | B2 * | 9/2009 | Villette | A61M 5/3286 604/264 |
| 8,568,422 | B2 * | 10/2013 | Morlet | A61F 9/00745 606/107 |
| 2006/0122458 | A1 * | 6/2006 | Bleich | A61B 17/1659 600/101 |
| 2008/0172033 | A1 * | 7/2008 | Keith | A61B 1/00154 604/506 |
| 2009/0264826 | A1 * | 10/2009 | Thompson | A61B 17/3207 604/164.13 |
| 2010/0087828 | A1 * | 4/2010 | Krueger | A61B 17/8811 606/93 |
| 2010/0331883 | A1 * | 12/2010 | Schmitz | A61B 10/0275 606/249 |
| 2011/0118658 | A1 | 5/2011 | Smith | |
| 2013/0131548 | A1 * | 5/2013 | McGhie | A61B 10/0266 600/567 |
| 2013/0310752 | A1 | 11/2013 | Kawaura | |
| 2014/0046303 | A1 * | 2/2014 | Donaldson | A61B 17/3415 604/540 |
| 2016/0143662 | A1 * | 5/2016 | Mulier | A61B 17/3496 606/49 |
| 2017/0087310 | A1 * | 3/2017 | Clement | A61M 13/003 |

OTHER PUBLICATIONS

Jaskille et al., "A Portable Handpump Is Effective in the Evacuation of Hemothorax in a Swine Model of Penetrating Chest Injury," *Journal of Trauma Injury, Infection, and Critical Care*, vol. 5(5), pp. 864-868, Nov. 2003.

Eckstein et al., "Needle thoracostomy in the prehospital setting," *Prehosp Emerg Care*, Apr.-Jun. 1998; 2(2):132-5.

Janicki, "The new sensor-equipped veress needle," *The Journal of the American Association of Gynecologic Laparoscopists*, Feb. 1994, vol. 1, Issue 2, pp. 154-156.

Warner et al., "Paramedic use of needle thoracostomy in the prehospital environment," *Prehosp Emerg Care*, Apr.-Jun. 2008; 12(2):162-168.

\* cited by examiner

MODIFIED VERESS NEEDLE FOR TENSION PNEUMOTHORAX DECOMPRESSION

CROSS REFERENCE TO RELATED APPLICATIONAPPLICATIONS

This is the U.S. National Stage of International Application No. PCT/US2014020027, filed Mar. 3, 2014, which was published in English under PCT Article 21(2), which in turn claims the benefit of U.S. Provisional Patent Application No. 61/771,442, filed Mar. 1, 2013, which is incorporated herein by reference in its entirety.

FIELD

The disclosure pertains to, inter alia, devices and methods for treating tension pneumothorax.

BACKGROUND

Tension pneumothorax (tension pneumothorax) is a life-threatening condition that is present in 0.2-1.7% of civilian trauma patients and up to 4% of battlefield casualties. This condition can result from a laceration of the lung, creating a parenchymal air leak with no means of evacuation. Consequently, the patient can manifest with severe hypoxia, hypercarbia, and/or cardiovascular collapse as increasing pressure in the hemithorax creates ipsilateral lung collapse and impedance of venous return to the heart.

Previous data from the Vietnam War suggested that up to 33% of preventable deaths on the battlefield resulted from tension pneumothorax. In civilian patients, the reported incidence of tension pneumothorax varies from 0.2% to 1.7%. In some cases, about 1.5% of blunt trauma patients can undergo needle decompression for suspected tension pneumothorax.

Despite its lethality, tension pneumothorax can be reversed with effective thoracic decompression. The current standard pre-hospital treatment of tension pneumothorax, as described in the $9^{th}$ edition of the Advance Trauma Life Support (ATLS) Student Course manual, is immediate decompression by inserting a large-caliber needle, most commonly a 5-cm 14-gauge angiocatheter, into the second intercostal space in the mid-clavicular line of the affected hemithorax. However, this technique has been repeatedly shown to be ineffective and unsafe, with failure rates ranging from about 40% to about 64%. Extrathoracic catheter placement and catheter kinking are the most commonly observed technical failures. Accordingly, improvements to devices and methods of treating tension pneumothorax are desirable.

WO2009068661 discloses a device for thoracostomy.

U.S. Pat. No. 5,971,960 discloses a trocar with expandable members for retaining the trocar.

U.S. Pat. No. 4,813,941 discloses a pneumo-thorax treatment device.

U.S. Pat. No. 6,742,519 discloses a medico-surgical apparatus.

U.S. Pat. No. 5,334,159 discloses a thoracentesis needle assembly utilizing check valve.

U.S. Pat. No. 7,229,433 discloses an apparatus for treating pneumothorax and/or hemothorax.

U.S. Pat. No. 4,447,235 discloses a thoracentesis device.

SUMMARY

Disclosed herein are representative devices and methods for treating tension pneumothorax. One aspect of this disclosure pertains to needle assemblies. In one representative embodiment, a needle assembly comprises an outer cannula defining a lumen and having a distal end portion comprising a sharp bevel, and an inner cannula slidably disposed in the lumen of the outer cannula. The inner cannula is movable between an extended position and a retracted position, and defines a lumen. The inner cannula also has a blunt distal end portion, which is configured to extend beyond the sharp bevel of the outer cannula when the inner cannula is in the extended position. The blunt distal end portion is also configured to be at least partially retracted within the lumen of the outer cannula when the inner cannula is in the retracted position, thereby exposing the sharp bevel. The needle assembly further comprises a housing coupled to a proximal end portion of the outer cannula, wherein the housing is configured to allow the inner cannula to travel through the housing. The lumen of the inner cannula can be accessible through an opening defined in the housing. The needle assembly further comprises a bias that positions the inner cannula relative to the outer cannula as appropriate during use of the needle assembly. In one embodiment the bias is a compression spring that is disposed inside the housing and coupled to the inner cannula such that the bias is in a less-compressed state when the inner cannula is in the extended position and in a more-compressed state when the inner cannula is in the retracted position. Thus, in the needle assembly, the extended position of the inner cannula is favored unless sufficient axial force is applied to the blunt distal end portion to cause the blunt distal end portion to move toward or be in the retracted position. During use of the needle to penetrate tissue such as a thoracic wall, as the needle is being urged into the tissue, the tissue applies an axial counter-force to the blunt distal end portion that favors the blunt distal end portion being in the retracted position (despite any force being applied by the bias). When penetration is complete, the tissue's counter-force drops substantially, which allows the bias to return the blunt distal end portion to the extended position, at which position the sharp bevel is rendered incapable of performing any further cutting or penetration. Thus, when the blunt distal end portion is in the retracted position, the sharp bevel of the outer cannula is exposed and available for penetrating and cutting tissue (as required, for example, when the device is being inserted into a patient). On the other hand, when the blunt distal end portion is in the extended position, the sharp bevel of the outer cannula is rendered thereby incapable of achieving further cutting or penetration of tissue. These changes from the retracted position to the extended position and vice versa occur automatically during use of the needle device, and give the user immediate tactile and visual feedback regarding depth and positioning of the needle in the patient, and regarding use of the device in a manner that does not cause any collateral trauma to the patient (other than the minimal trauma necessary for the needle assembly to penetrate into the patient).

Another aspect of this disclosure pertains to methods, wherein a representative embodiment is directed to a method of treating tension pneumothorax in a patient or animal subject. The method comprises contacting a Veress-type needle assembly to a desired penetration site on a patient. The device is urged by the user to penetrate into the patient's thoracic cavity, which applies a corresponding force to the blunt distal end of the inner cannula that urges movement of the blunt distal end portion to a retracted position. When penetration of the needle through the thoracic cavity is complete, the pressure being applied to the blunt distal end of the inner cannula is correspondingly reduced, which allows the inner cannula to move automatically to an extended position at which the sharp bevel of the outer cannula is prevented from further cutting or penetration of the tissue. The user is made aware of this change from the retracted position to the extended position by tactile feedback from the needle assembly to the user and visually by observing motion of the proximal end portion of the inner cannula into the housing. The needle assembly can then be used for, e.g., withdrawing fluid from the thoracic cavity through the lumen of the inner cannula.

DETAILED DESCRIPTION

Figure 1:
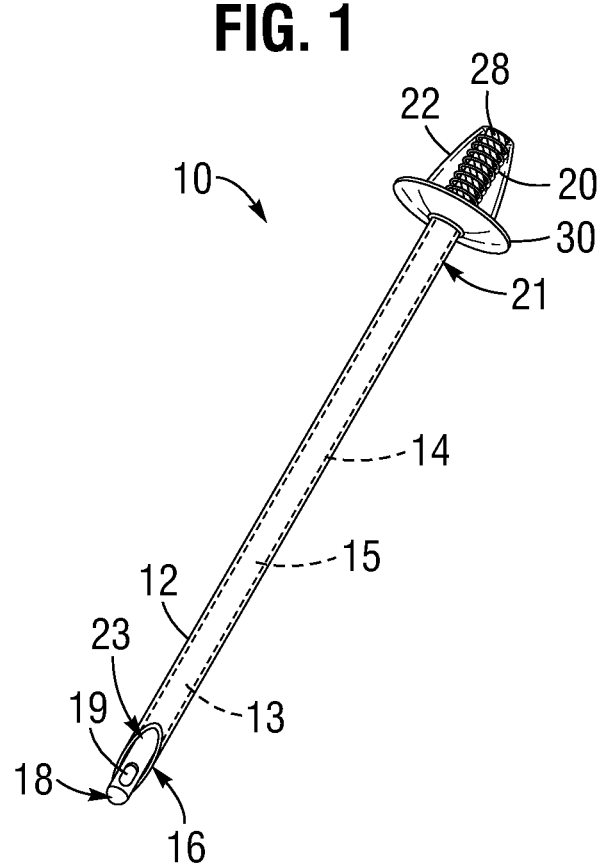
FIG. 1 is a perspective view of an embodiment of a modified Veress needle assembly.
Figure 2:
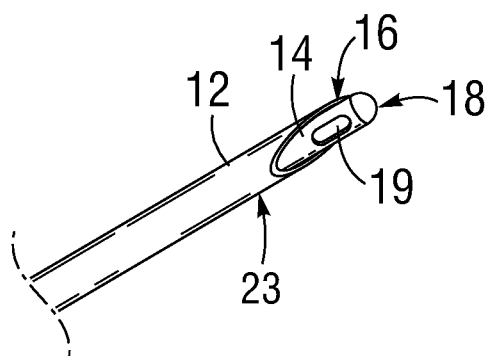
FIG. 2 is a detailed view of the needle assembly of FIG. 1 with an inner cannula in an extended position.
Figure 3:
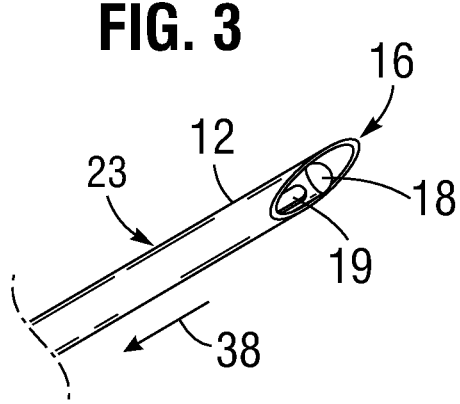
FIG. 3 is a detailed view of the needle assembly of FIG. 1 with the inner cannula in a retracted position.

This disclosure is set forth in the context of representative embodiments that are not intended to be limiting in any way.

As used herein, the singular forms "a," "an," and "the" include the plural forms unless the context clearly dictates otherwise. Additionally, the term "includes" means "comprises." Further, the term "coupled" encompasses mechanical as well as other practical ways of coupling or linking items together, and does not exclude the presence of intermediate elements between the coupled items.

The things and methods described herein should not be construed as being limiting in any way. Instead, this disclosure is directed toward all novel and non-obvious features and aspects of the various disclosed embodiments, alone and in various combinations and sub-combinations with one another. The disclosed things and methods are not limited to any specific aspect or feature or combinations thereof, nor do the disclosed things and methods require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and method. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In the following description, certain terms may be used such as "up," "down,", "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Referring to FIGS. 1-5, an embodiment of a needle assembly configured as a modified Veress needle 10 is shown. The needle assembly 10 comprises an outer cannula 12 defining a first lumen 13, and an inner cannula 14 disposed through the first lumen 13 of the outer cannula 12. The inner cannula 14 is thereby coaxial with the outer cannula 12. The outer cannula 12 has a proximal end portion 21 and a distal end portion 23, the distal end portion 23 including a sharp bevel 16 configured, when exposed, to pierce the tissue of a body cavity of a patient when sufficient force is applied the outer cannula by a user. The inner cannula 14 defines a second lumen 15, and has a blunt distal end portion 18 including an opening 19. The opening 19 is in communication with the second lumen 15 of the inner cannula 14. The inner cannula 14 is also coupled to a bias mechanism configured, in this embodiment, as a spring 20. The inner cannula 14 is configured to move between an extended position (FIGS. 1 and 2) and a retracted position (FIGS. 3 and 5) corresponding to a less-compressed state and a more-compressed state of the spring 20, respectively. Whenever the inner cannula 14 is in the retracted position, the sharp bevel 16 is in an "exposed" condition in which it can pierce tissue. Whenever the inner cannula 14 is in the extended position, the sharp bevel 16 is in an ineffective condition for piercing tissue.

The needle assembly 10 is configured such that, when the inner cannula 14 is in the extended position, the blunt distal end portion 18 protrudes beyond the sharp bevel 16 of the outer cannula 12, thereby rendering the sharp bevel 16 ineffective for piercing body tissue. However, whenever the blunt distal end portion 18 is pressed against, for example, the tissue of a body cavity, a resistance force is applied by the tissue against the blunt distal end portion 18. This resistance force can cause the spring 20 to compress. Sufficient compression of the spring 20 causes the blunt distal end portion 18 of the inner cannula 14 to travel inside the first lumen 13 of the outer cannula 12 in a retractive manner, thereby exposing the sharp bevel 16 for use in piercing body tissue. In this manner, the modified Veress needle 10 can be driven through the tissue of a body cavity by simply pressing the needle 10 against the tissue. Upon completing the piercing of the body cavity, the resistance pressure previously applied to the inner cannula 14 by the tissue is reduced, allowing the spring 20 to move the inner cannula 14 in the lumen 13 of the outer cannula 12 to the extended position, thereby rendering the sharp bevel 16 ineffective.

Figure 4A:
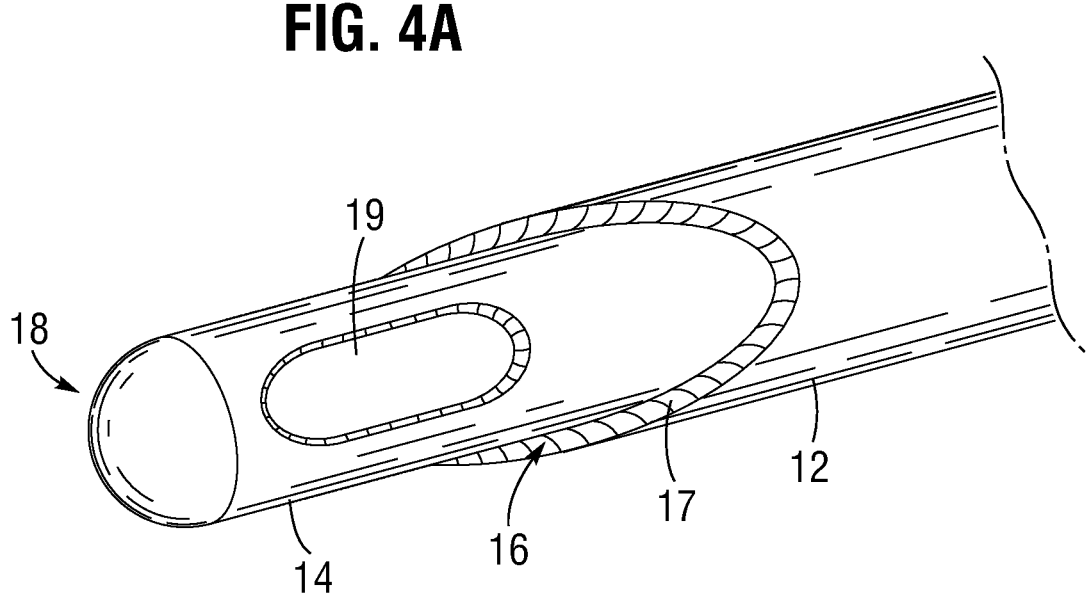
FIG. 4A is a detailed perspective view of a distal end portion of the needle assembly of FIG. 1.
Figure 4B:
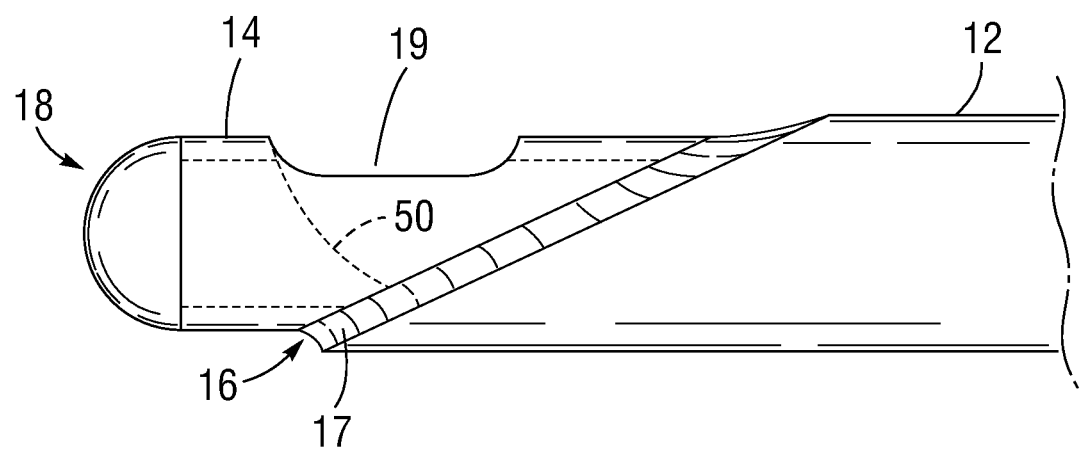
FIG. 4B is a detailed cross-sectional side-elevation view of the distal end portion of the needle assembly of FIG. 1.

Referring to FIGS. 4A and 4B, the sharp bevel 16 of the outer cannula 12 desirably is beveled such that an edge surface 17 of the bevel 16 is radiused, and curves away from the surface of the inner cannula 14 whenever the inner cannula 14 is in the extended position. The radius of the surface 17 of the sharp bevel 16 is configured such that, whenever the inner cannula 14 is in the extended position, tissue that comes in contact with the blunt distal end portion 18, or directly in contact with the sharp bevel 16, is urged along the edge surface 17 of the sharp bevel 16 without being pierced or cut by the sharp bevel 16. In this manner, the blunt distal end portion 18 of the inner cannula 14 renders the sharp bevel 16 ineffective for piercing or cutting tissue when the inner cannula 14 is in the extended position. In alternative embodiments, the edge surface 17 of the sharp bevel 16 need not be radiused, but can instead define an angle with the surface of the inner cannula 14 such that tissue is urged along the sharp bevel 16 without being cut by the sharp bevel 16, as described above.

Figure 5:
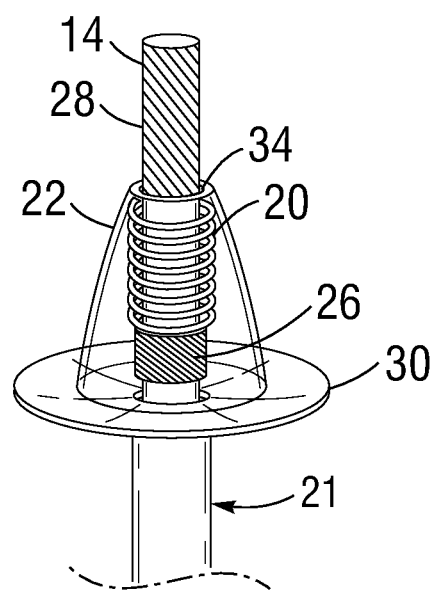
FIG. 5 is a detailed side elevation view of a housing of the needle assembly of FIG. 1.

Referring to FIG. 5, the needle assembly 10 can comprise a housing 22 having a cylindrical or frustroconical shape. The housing 22 can be coupled to the outer cannula 12 by a collar 30. The housing 22 is configured such that, when the inner cannula 14 is in the retracted position, a proximal end portion 28 of the inner cannula 14 extends from the housing 22 through an opening 34 defined in the housing 22. The proximal end portion 28 of the inner cannula 14 can comprise a color or visual pattern on its surface such that, when the inner cannula 14 is in the retracted position, the proximal end portion 28 serves as a visual indicator, indicating to a user that the sharp bevel 16 of the outer cannula 12 is exposed. Conversely, when the inner cannula 14 is in the extended position, the proximal end portion 28 is located at least partially inside the housing 22, indicating that the sharp bevel 16 is ineffective for piercing tissue. In the embodiment shown, the housing 22 is transparent, which allows a user to view inside the housing 22. In alternative embodiments, the housing 22 can be opaque, partially transparent, or can have a transparent portion, as desired.

In the depicted embodiment, the spring 20 is contained in the housing 22, and is coupled to the inner cannula 14 by a spring retainer 26. The spring retainer 26 is configured to compress the spring 20 as the inner cannula 14 is moved to the retracted position (for example, when pressure is applied to the blunt distal end portion 18), and to decompress the spring 20 accompanying motion of the inner cannula 14 to the extended position (e.g., when the applied pressure is reduced). The spring retainer 26 can be configured to move with the inner cannula 14 inside the lumen 13 of the outer cannula 12 such that, when the inner cannula 14 is in the extended position, the spring retainer 26 is located inside the lumen 13 of the outer cannula 12. Similarly, when the inner cannula 14 is in the retracted position, the spring retainer 26 is located in the housing 22 where it can serve as a visually distinguishable feature visible to a user through the transparent housing 22, as shown in FIG. 5. In this manner, the spring retainer 26 can serve as an additional visual indicator to a user that the sharp bevel 16 is exposed and the inner cannula 14 is in the retracted position.

The opening 34 defined by the housing 22 can allow a user to access the lumen 15 of the inner cannula 14 regardless of whether the inner cannula 14 is in the extended or the retracted position. Thus, the lumen 15 of the inner cannula 14 can be used as a conduit for introducing any of various instruments, such as guide wires, catheters, etc., into the body cavity pierced by the needle 10. In some embodiments, the lumen 15 of the inner cannula 14 has a diameter of about 3 mm, which can allow the modified Veress needle 10 to more effectively pass air and/or liquids from the body cavity or to the body cavity.

Figure 6:
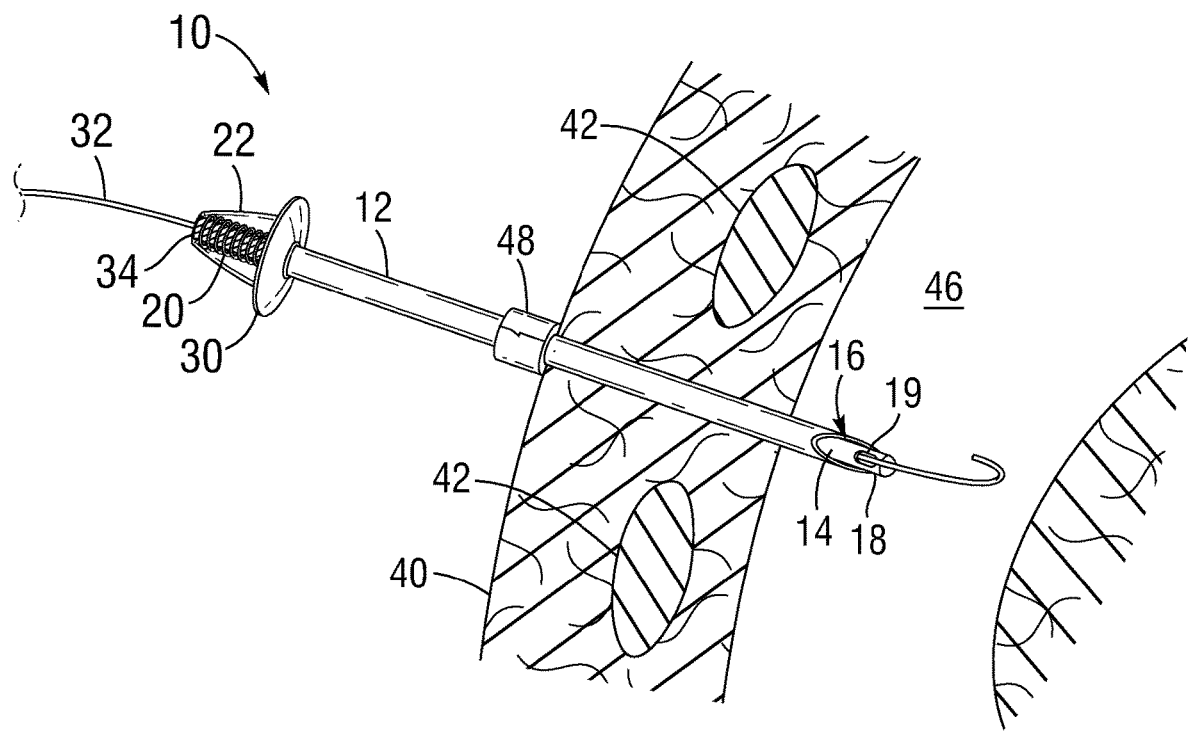
FIG. 6 is a cross-sectional side elevation view of a thoracic cavity showing a needle assembly inserted through the thoracic wall and having a guide wire threaded through an inner cannula.
Figure 7:
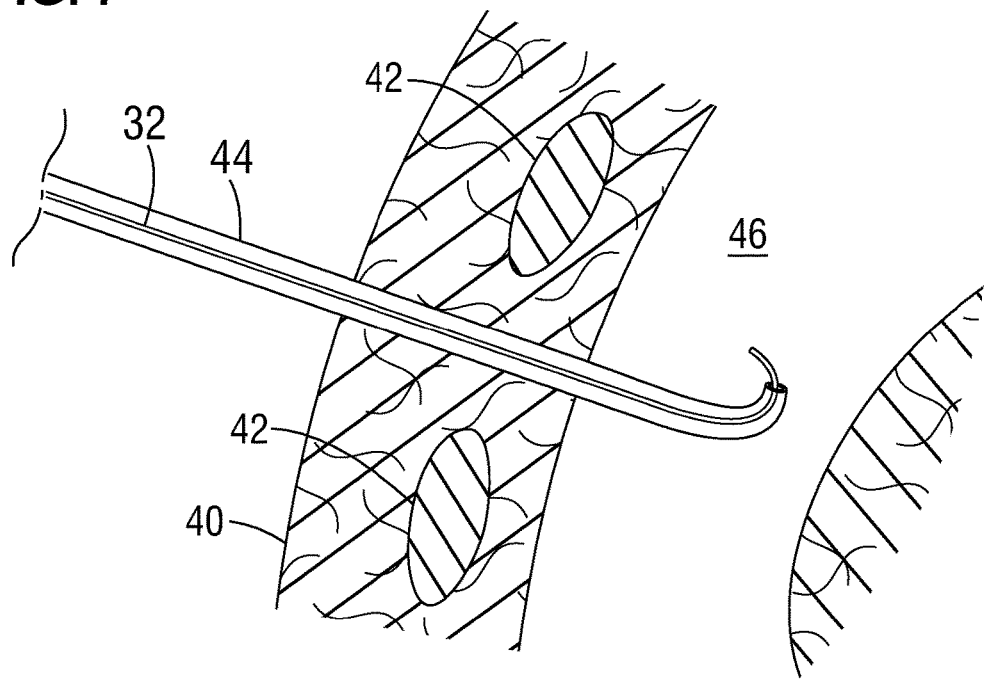
FIG. 7 is a cross-sectional side elevation view of the thoracic wall of FIG. 5 showing a pigtail catheter inserted into the thoracic cavity along the guide wire.

Referring now to FIGS. 6 and 7, the modified Veress needle 10 can be employed to treat, for example, tension pneumothorax. In an exemplary protocol, the modified Veress needle 10 is advanced through thoracic tissues into a thoracic cavity 46 by pushing the needle 10 through the thoracic wall 40 between ribs 42. As the distal end portion 18 is urged against the thoracic wall 40, the tissue of the thoracic wall 40 bears on the blunt distal end portion 18 of the inner cannula 14, thereby moving the inner cannula 14 rearwardly and compressing the spring 20. Compression of the spring 20 accompanies movement of the inner cannula 14 to the retracted position, in which the proximal end portion 28 of the inner cannula 14 extends from the housing 22 (see FIG. 5). Thus, the user is notified that the sharp bevel 16 is exposed, as described above. Upon completing the piercing of the thoracic cavity wall 40, resistance force applied to the inner cannula 14 is substantially reduced, which allows the spring 20 to decompress. This decompression of the spring 20 allows the inner cannula 14 to move to the extended position as the proximal end portion 28 correspondingly moves inside the housing 22, indicating to the user that the sharp bevel 16 is ineffective. At this time, further advancement of the needle assembly 10 into the thoracic cavity 46 can be halted, and the opening 19 in the blunt distal end portion 18 of the inner cannula 14 can be exposed. Any of various fluids such as air, blood, puss, etc., in the thoracic cavity 46, can now be withdrawn from the thoracic cavity 46 through the opening 19 into the lumen 15 of the inner cannula 14 and out of the body.

Some embodiments include a pierce-depth limiter 48 secured to the outer cannula 12, shown configured as a flange in FIG. 6. The pierce-depth limiter 48 is attached to the outer cannula 12 at a location that prevents the needle 10 from extending too deeply into the tissue. As the modified Veress needle 10 is urged progressively further into the thoracic cavity 46, the pierce-depth limiter 48 ultimately contacts the exterior tissue of the thoracic wall 40. In such a state, the pierce-limiter 48 prevents the modified Veress needle 10 from penetrating further into the thoracic cavity 46.

Figure 8:
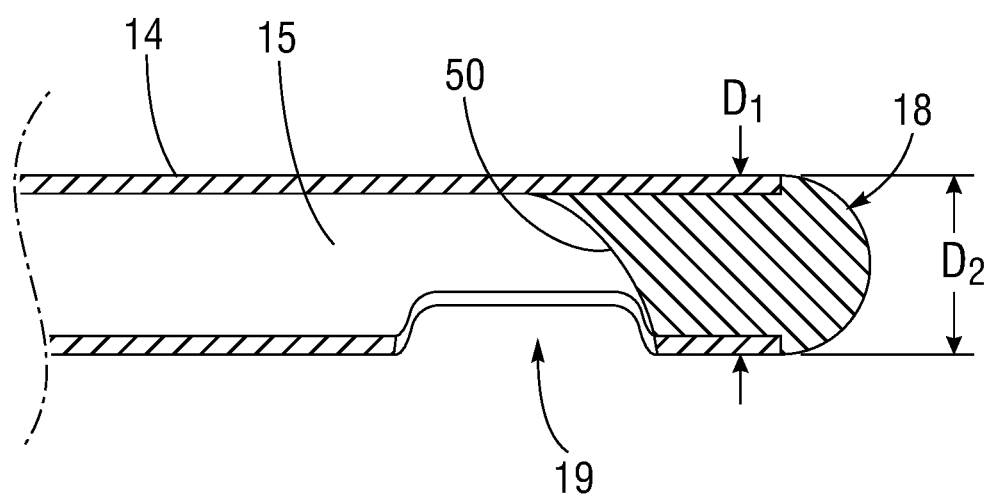
FIG. 8 is a sectional view of a distal end portion of an inner cannula illustrating a curved surface configured to guide a wire out of an opening in the inner cannula.

Still referring to FIG. 6, after the modified Veress needle 10 has been inserted into the thoracic cavity, a guide wire 32 can be inserted through the proximal end portion 28 into the lumen 15 (see FIG. 1) of the inner cannula 14. The lumen 15 defines a route through which the guide wire 32, or any other suitable instrument, can be routed into or out of the body cavity. The guide wire 32 can then be threaded through the opening 19 into the thoracic cavity 46. In some embodiments, the blunt distal end portion 18 comprises a curved interior surface 50 configured to urge the guide wire 32 through the opening 19, as shown in FIG. 8. Once the guide wire 32 has been threaded through the opening 19, the modified Veress needle 10 can be withdrawn from the tissue, leaving the guide wire 32 behind, extending through the thoracic wall 40.

The guide wire 32 facilitates insertion of any of various instruments into the thoracic cavity 46 along the guide wire 32. For example, a pigtail catheter 44, such as a Cook Medical Sof-Flex® Ileal Conduit Pigtail Catheter, can be threaded along the guide wire 32 into the thoracic cavity 46 for drainage or irrigation of the cavity, as shown in FIG. 7. Once the pigtail catheter 44 is in place extending through the thoracic wall 40, the guide wire 32 can be removed. Alternatively, or in addition, other instruments such as chest tubes, etc., can be introduced into the thoracic cavity 46 along the guide wire 32. The modified Veress needle 10 can also be used for performing various other procedures, including accessing the intra-abdominal cavity for laparoscopy, or for performing various percutaneous procedures, such as thoracic or intra-abdominal percutaneous drainages. In some embodiments, the needle assembly 10 can be attachable to a valve or fitting, such as a stopcock, for introduction or withdrawal of fluids to or from the thoracic cavity, respectively.

In the embodiment depicted, the blunt distal end portion 18 is dome-shaped, by which is meant that an outer diameter $D_1$ of the inner cannula 14 is approximately equal to a diameter $D_2$ of the blunt distal end portion 18, as shown in FIG. 8. In this manner, the blunt distal end portion 18 can help to deflect tissue around the needle assembly 10 as the needle assembly 10 pierces the tissue of a body cavity. However, in alternative embodiments, the blunt distal end portion 18 can have a diameter $D_2$ that is less than the outer diameter $D_1$ of the inner cannula 14, and the edges of the inner cannula 14 can be rounded or beveled so as to urge tissue along the interface between the blunt distal end portion 18 and the inner cannula 14 without being cut or pierced. In further alternative embodiments, the blunt distal end portion 18 need not be domed, but can have any suitable shape. For example, the blunt distal end portion 18 can have a flattened configuration wherein the edges of the blunt distal end portion 18 and/or the inner cannula 14 are beveled or rounded. The blunt distal end portion 18 can also be faceted, as desired.

In some embodiments, the blunt distal end portion 18 is integrally formed with the inner cannula 14. As used herein, "integrally formed" refers to a construction that does not include any welds, fasteners, or other means for securing separately formed pieces of material to each other. In alternative embodiments, the inner cannula 14 and the blunt distal end portion 18 can be separately formed and secured together by, for example, welding, brazing, adhesive, etc.

The modified Veress needle 10 has several configurational and functional advantages compared to a conventional 14-gauge thoracostomy needle for the treatment of tension pneumothorax. The design and functional advantages of the modified Veress needle 10 include: (1) longer needle length (e.g., 14 cm modified Veress needle 10 compared to a conventional 5 cm thoracostomy needle); (2) a large bore diameter of the lumen 15 of the inner cannula 14 (e.g., 3 mm for the modified Veress needle 10 compared to 1.5 mm for a conventional thoracostomy needle); (3) tactile and visual feedback of parietal pleura penetration (e.g., using the proximal end portion 28 of the inner cannula 14 and/or the spring retainer 26); (4) the sharp bevel 16 is rendered ineffective for further tissue cutting or piercing by the blunt distal end portion 18 of the inner cannula 14 once the needle 10 is inserted in the tissue; (5) no need for use of plastic sheaths, which reduces the risk of kinking; and (6) ability to pass a wire (such as guide wire 32) through the lumen 15 of the inner cannula 14 to guide placement of a pigtail catheter.

Additional features of the modified Veress needle 10 compared to the conventional Veress needles, are: (1) a material such as masking tape placed on the inner cannula 14 can serve to limit the length of extension of the blunt distal end portion 18 out of the outer cannula 12; (2) visual indication that the sharp bevel 16 is exposed is provided by the proximal end portion 28 of the inner cannula 14; and (3) a wire can be passed from the proximal end of the inner cannula 14 and out through the opening 19 to guide, for example, pigtail catheter placement using the Seldinger technique.

Figure 9:
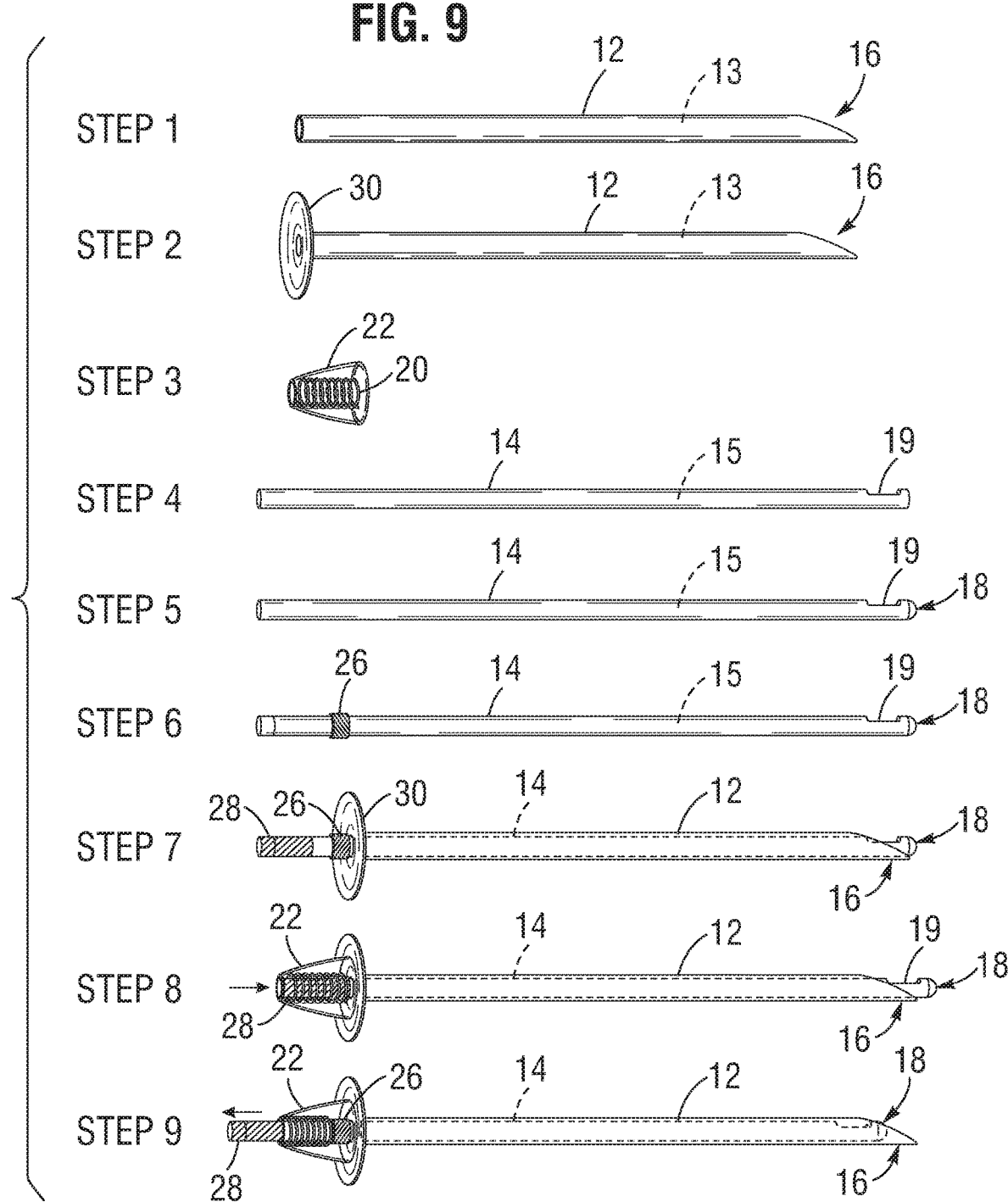
FIG. 9 is a schematic of a method of assembly of an alternative embodiment of a needle assembly.

The following steps of an exemplary method for constructing a modified Veress needle are shown in FIG. 9. In a first step, the outer cannula 12 is cut to a desired length (e.g., 10 cm) and one tip beveled using, for example, a Dremmel tool, to form the sharp bevel 16. In a second step, the outer cannula 12 is coupled to the collar 30 (e.g., at a 90-degree angle). In some examples, the collar 30 is a ¾" diameter steel plate with a central hole. In a third step, the housing 22 is configured having a length of, for example, 3 cm. In some embodiments, the housing 22 is fashioned from, for example, a unit of tubing normally used for forming ink-pen casings. In some examples, the inner spring of the pen can be used as the spring 20. In a fourth step, the opening 19 is cut in the inner cannula 14. The opening 19 can be located about, for example, 0.5 cm from tip of the inner cannula 14, or at any other suitable distance from the tip of the inner cannula 14. The blunt distal end portion 18 of the inner cannula 14 can then be formed of, for example, any biocompatible metal or plastic. In the embodiment shown, and described above, the blunt distal end portion 18 extends radially outward from the inner cannula 14 on the same side of the inner cannula 14 as the opening 19. In alternative embodiments, the blunt distal end portion 18 and the opening 19 are included on the inner cannula 14 during initial fabrication, thereby eliminating the need for later modification of the inner cannula 14.

In a sixth step, the spring retainer 26 is applied to the inner cannula 14, e.g. about 3.5 cm from the end of the inner cannula 14 on the side opposite the opening 19. In some embodiments, the spring retainer 26 moves with the inner cannula 14 such that the spring retainer 26 is visible through the housing 22 to a user when the inner cannula 14 is in the retracted position, and hidden from view by the outer cannula 12 when the inner cannula 14 is in the extended position. The spring retainer 26 can be configured to compress the spring 20 when the inner cannula 14 is in the retracted position. In some embodiments, the spring retainer 26 can be configured as a collar made of, for example, metal or plastic, or as a thin adhesive tape layer (e.g., masking tape). In some embodiments, the spring retainer 26 can have a thickness of about 0.3 cm. In this manner, the spring retainer 26 can have a circumference sufficiently small such that it can travel within the inner diameter of the housing 22 and the lumen 13 of the outer cannula 12 without binding, yet is large enough to retain and compress the spring 20 in the housing 22.

In a seventh step, the inner cannula 14 is inserted into the lumen 13 of the outer cannula 12 such that the blunt distal end portion 18 protrudes past the sharp bevel 16 of the outer cannula 12. A visual pattern can be applied to the proximal end portion 28 of the inner cannula 14 to provide visual detection of the proximal end portion.

In an eighth step, the spring 20 is placed over the proximal end portion 28 of the inner cannula 14.

In a ninth step, the housing 22 is placed over the spring 20. In some embodiments, this step can result in slight compression of the spring 20. The housing 22 can then be coupled to the collar 30 by, e.g., adhesive, welding, brazing, etc. Alternatively, or in addition, a color or visual pattern can be applied to the proximal end portion 28 of the inner cannula 14 such that when the sharp bevel 16 is exposed, the colored proximal end portion 28 of the inner cannula 14 is visible to a user.

EXAMPLE 1

The current pre-hospital standard of care using a conventional large-bore intravenous catheter for tension pneumothorax decompression is associated with a high failure rate. The modified Veress needle 10 was developed to treat this condition. In this example, the effectiveness of the modified Veress needle 10 was evaluated against the effectiveness and safety of a 14-gauge needle thoracostomy in a swine tension pneumothorax model.

In a randomized cross-over swine model of 43 tension pneumothorax events, use of the modified Veress needle 10 resulted in 100% successful tension decompressions within 70±86 seconds, with no deaths. The modified Veress needle 10 also exhibited 100% successful rescues of 11 events crossed-over to the modified Veress needle 10, in which needle thoracostomy resulted in 21% successful decompressions within 157±96 seconds. 21% deaths resulted from unsuccessful tension pneumothorax decompressions using conventional needles, and 11/19 events necessitated cross-over to the modified Veress needle 10 due to failure to restore 80% baseline systolic blood pressure within 5 minutes, using conventional needles.

Tension pneumothorax was created in sixteen adult swine via thoracic $CO_2$ insufflation to 15 mmHg. After tension physiology was achieved, defined as a 50% reduction of cardiac output (CO), the swine were randomized to undergo compression using either the modified Veress needle 10 or a conventional thoracostomy needle. Failure to restore 80% baseline SBP within 5 minutes resulted in crossover to the alternate device (i.e., use of a modified Veress needle 10 instead of a conventional thoracostomy needle, or vice versa). The success rate of each device, death of subject, and needs for crossover were analyzed using Chi-square.

Forty-three tension events were created in 16 swine (24 using the modified Veress needle 10, and 19 using a thoracostomy needle) at 15 mmHg intrathoracic pressure with a mean $CO_2$ volume of 3.8 liters. Tension pneumothorax resulted in a 48% decline of SBP from baseline and 73% decline of CO. 42% of induced tension pneumothorax events had equalization of central venous pressure with pulmonary capillary wedge pressure. All tension events randomized to use of the modified Veress needle 10 were successfully rescued within an average 70±86 seconds. Use of conventional needle thoracostomy resulted in 4 (21%) successful decompressions within an average 157±96 seconds. Four swine (21%) died within 5 minutes of decompression using conventional needle thoracostomy. The persistent tension events where the swine survived past 5 minutes (11/19 needle thoracostomy) underwent crossover to decompression with the modified Veress needle 10, which yielded 100% rescue. Neither the modified Veress needle 10 nor the needle thoracostomy was associated with inadvertent injuries to the viscera.

Thoracic insufflation produced a reliable and highly reproducible model of tension pneumothorax. The modified Veress needle 10 was greatly superior to the conventional thoracostomy needle for effective and safe tension pneumothorax decompression and physiologic recovery.

In this example, the modified Veress needle 10 included a spring-loaded, hollow, blunt-tip inner cannula 14 (e.g., having a length of 14 cm and a diameter 4.5 mm) situated inside an outer cannula 12 (e.g., having a length of 10 cm and a diameter 3.5 mm). During insertion, the tissue resistance pushed back the inner cannula 14 by compressing the spring 20, thus exposing the sharp bevel 16 of the outer cannula 12 to cut through tissues, as described above. Once the needle 10 entered the thoracic cavity, the loss of tissue resistance allowed the spring 20 to decompress and extend the blunt distal end portion 18 of the inner cannula 14 beyond the sharp bevel 16 of the outer cannula 12, thus protecting the viscera from injury.

A visual "needle exposed" indicator feature was included in the modified Veress needle 10 to assist the operator in safe placement of the needle. Protrusion of the proximal end portion 28 of the inner cannula 14 through the opening 34 of the housing 22 was linked to compression of the spring 20 which, in turn, indicated exposure of the sharp bevel 16. After tissue resistance substantially decreased, such as encountered when the modified Veress needle 10 entered the thoracic cavity, the decompression of the spring 20 caused the proximal end portion 28 of the inner cannula 14 to move inside the housing 22 such that the proximal end portion 28 no longer protruded from the housing 22.

In this randomized cross-over swine model of 43 tension pneumothorax events, the modified Veress needle 10 exhibited 100% successful tension decompression within 70±86 seconds, no deaths, and 100% successful rescues of the 11 events crossed-over to the modified Veress needle 10. Needle thoracostomy resulted in: (a) 21% successful decompression within 157±96 seconds, (b) 21% deaths from unsuccessful tension pneumothorax decompressions, and (c) 11/19 events necessitating cross-over due to failure to restore 80% baseline systolic blood pressure within 5 minutes.

EXAMPLE 2

In this example, a randomized crossover study of tension pneumothorax treated by modified Veress needle 10 or conventional 14-gauge needle thoracostomy (NT) in 16 adult Yorkshire swine was performed. The experiments were performed in accordance with the animal research guidelines of the University of Arizona's Institutional Animal Care and Use Committee (IACUC). Swine, weighing between 150 lbs to 250 lbs, were endotracheally intubated and anesthetized with a combination of ketamine (15 mg/kg), xylazine (2.2 mg/kg), and isoflurane (1-4%). Animals were then placed on volume-controlled mechanical ventilation with a 10 mL/kg tidal volume.

All swine were monitored with continuous electrocardiography and pulse oximetry. The internal jugular vein and common carotid artery were exposed under sterile conditions and cannulated for invasive hemodynamic monitoring using arterial line and pulmonary artery catheters. Baseline hemodynamics were recorded including heart rate, oxygen saturation, systolic blood pressure (SBP), central venous pressure (CVP), pulmonary artery pressure (PAP), pulmonary capillary wedge pressure (PCWP), and cardiac output (CO).

A 5-mm thoracoscopic trocar was inserted into the right chest along the mid-axillary line at the level of the highest nipple. The trocar was connected to a $CO_2$ insufflator for infusion at 2 L/min and continuous intrathoracic pressure monitoring. Intrathoracic pressures of 5, 10 and 15 mmHg were sequentially established. At each pressure (5, 10, 15 mmHg), animals were allowed to acclimate for 1 minute and all hemodynamics were then recorded. Tension physiology, defined for the purposes of this experiment as a 50% reduction of CO from baseline, was universally reached at 15 mmHg. Total $CO_2$ infused was then recorded.

Animals were randomized to group assignment (modified Veress needle 10 or needle thoracostomy) by blinded selection of pre-labeled index cards. The modified Veress needle 10 or thoracostomy needle was inserted percutaneously into the third intercostal space midway between the forelimbs and sternum thereby simulating the mid-clavicular line in humans (swine do not have clavicles). In swine randomized to needle thoracostomy, the needle was then removed, leaving the plastic catheter sheath traversing through the anterior chest wall. During decompression, $CO_2$ insufflation was continued at 1 L/min to simulate an ongoing air leak.

After placement of the assigned device (modified Veress needle 10 or needle thoracostomy), tension pneumothorax decompression was allowed to proceed for a maximum of 5 minutes. Hemodynamics were measured at 1, 3, and 5 minutes after device insertion. Successful decompression was defined as a return of SBP to 80% of baseline within this time frame. Failure to decompress within 5 minutes prompted thoracoscopic inspection of the device in-situ, and reasons for failure were recorded. The randomized device was then removed and the crossover device inserted in the aforementioned location. Hemodynamic parameters were measured at 1, 3, and 5 minutes. At the end of the experiment, the device was inspected with the thoracoscope before its removal. Those animals successfully decompressed were allowed to acclimate for 5 minutes, and the experiment was repeated for a maximum of 3 times per animal.

The tension events of the 16 swine were grouped according to the decompression device (i.e., the modified Veress needle 10 or the needle thoracostomy). A non-parametric analysis (Mann-Whitney U) was utilized to explore the differences in continuous variables (time to successful decompression) between groups. A Pearson chi-square analysis was utilized to explore for differences in categorical variables (crossover and survival). P-values <0.05 were significant.

Figure 10:
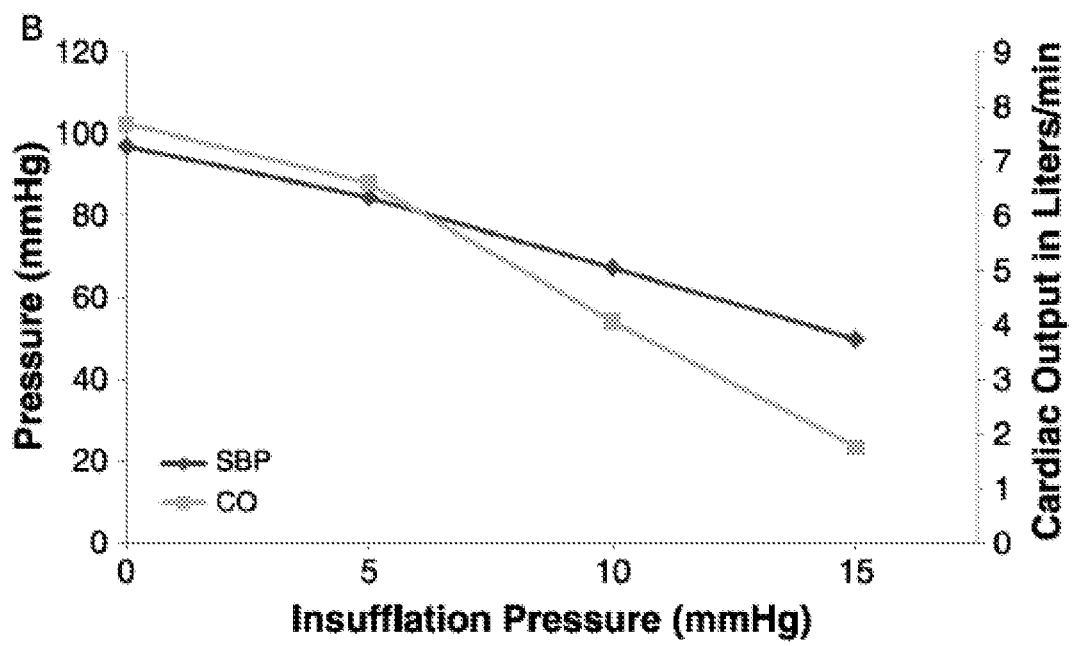
FIG. 10 is a plot of pressure versus insufflation pressure for systolic blood pressure and cardiac output.
Figure 11:
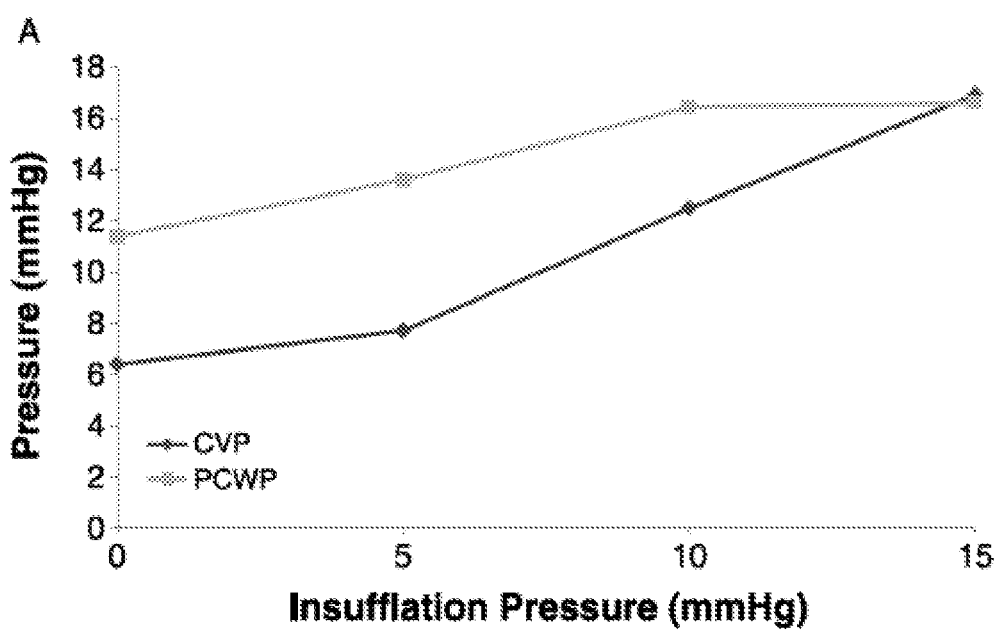
FIG. 11 is a plot of pressure versus insufflation pressure for central venous pressure and pulmonary capillary wedge pressure.

Forty-three (n=43) tension events were created in 16 swine, 24 events in the modified Veress needle 10 group and 19 events in the needle thoracostomy group. All swine had a decline in SBP and CO from baseline with an average of 48% and 73%, respectively (FIG. 10). CVP and PCWP equalized in 42% of events (FIG. 11). The average amount of $CO_2$ to reach tension was 3.8 liters.

Figure 12:
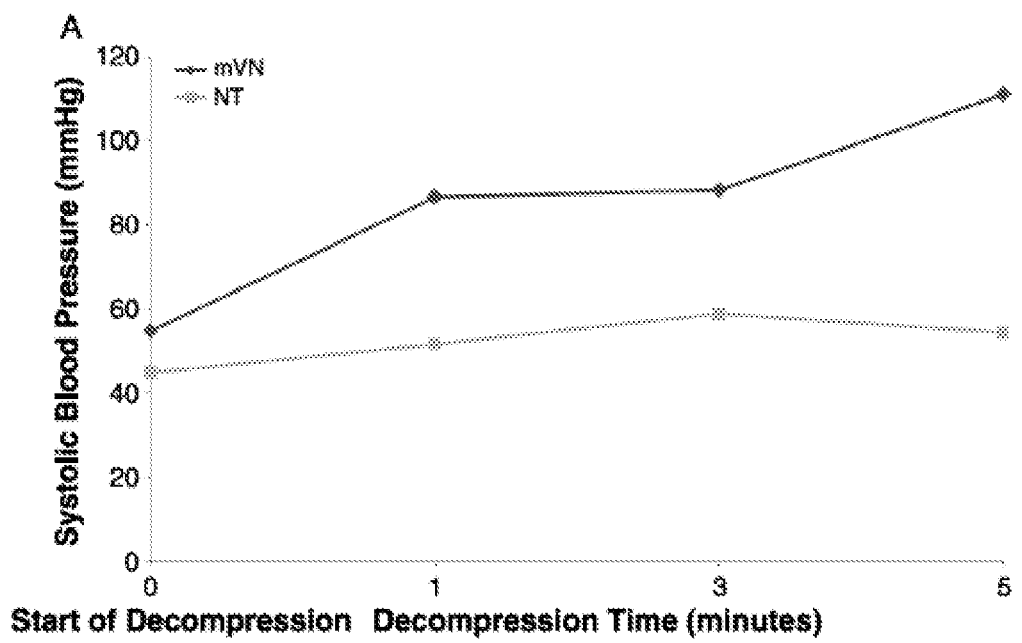
FIG. 12 is a plot of systolic blood pressure versus decompression time for tension pneumothorax decompression with a modified Veress needle and a thoracostomy needle.
Figure 13:
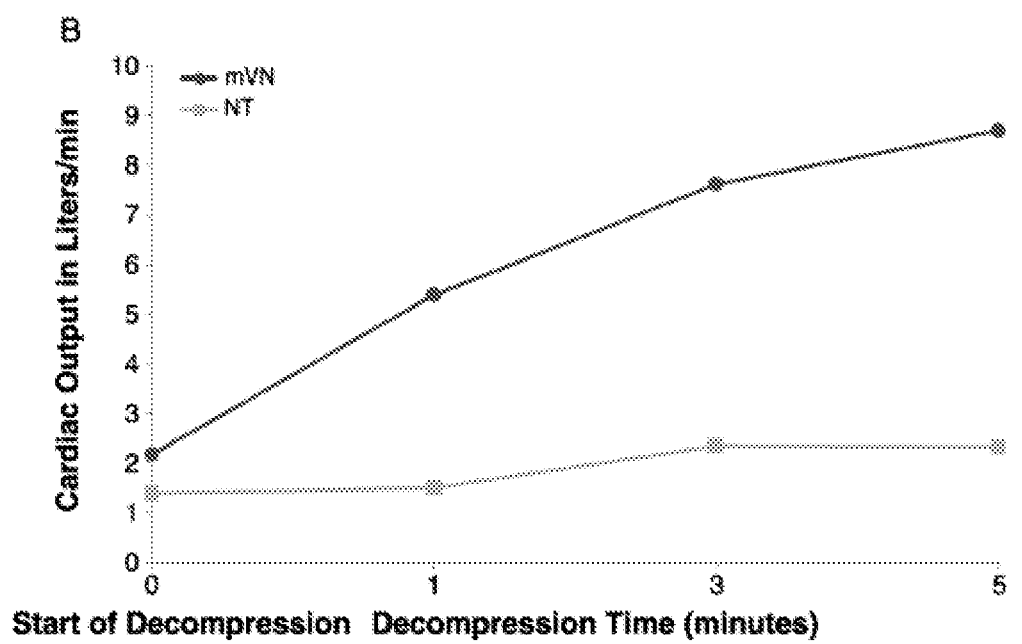
FIG. 13 is a plot of cardiac output versus decompression time for tension pneumothorax decompression with a modified Veress needle and a thoracostomy needle.
Figure 14:
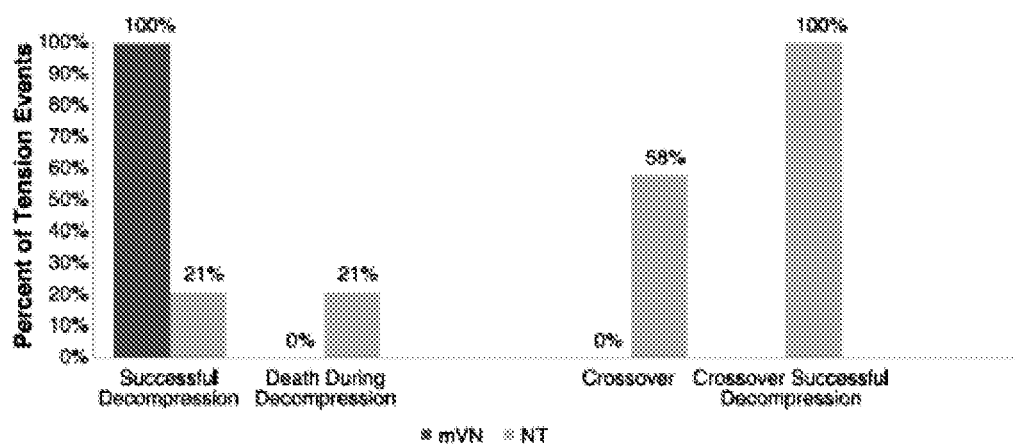
FIG. 14 is a chart illustrating the percentage of successful decompression events, required cross-overs, successful cross overs, and deaths for tension pneumothorax decompression performed with a modified Veress needle and a thoracostomy needle.

In the modified Veress needle group, 24 (100%) tension events were successfully decompressed with a mean time of 70±86 seconds. For tension events randomized to needle thoracostomy, 4 (21%) events were successfully decompressed (p<0.001) with a mean time of 157±96 seconds. The P-value for mean time from decompression to successful rescue between the modified Veress needle 10 and needle thoracostomy was 0.08. Four (21%) tension events randomized to needle thoracostomy resulted in swine death within 5 minutes, before crossover could take place. Eleven (58%) of the needle thoracostomy tension events required crossover to modified Veress needle, which resulted in subsequent 100% successful decompression (FIGS. 12, 13, and 14).

The 15 tension events that failed decompression by conventional needle thoracostomy underwent device inspection via thoracoscopy immediately prior to crossover in order to determine the reasons for failure. Catheter migration/dislodgement out of the thoracic cavity accounted for 7 (46%) failures. Four (27%) catheters were kinked. Four catheters (27%) appeared patent and in the proper location, but did not produce adequate $CO_2$ evacuation to achieve hemodynamic recovery.

In this example, the performance of the modified Veress needle was superior to 14-gauge needle thoracostomy in the decompression of tension pneumothorax. Additionally, the modified Veress needle 10 successfully rescued those animals with tension pneumothorax when the 14-gauge catheters failed.

The modified Veress needle 10 was successful in this example because it addressed five shortcomings of the conventional thoracostomy needle: (1) inadequate length, (2) small bore diameter, (3) blind sharp needle insertion, (4) lack of tactile or visual feedback, and (5) plastic sheath composition.

The typical length of a 14-gauge angiocatheter in common field use is 5 cm. Several cadaver and CT based studies revealed that, in humans, the average anterior chest wall thickness (CWT) over the second intercostal space along the mid-clavicular line is 4.5 cm, and 25-33% of patients have CWT>5 cm. The lack of sufficient catheter length to compensate for patient movement and catheter migration contributes to the high failure rate observed in the field.

The inner bore diameter of a conventional 14-gauge angiocatheter is 1.6 mm. Calculation based on the Bernoulli equation shows a flow rate of 2.6 L/min (length 5 cm, diameter 1.6 mm, pressure gradient 5 mmHg). The combination of air leak resulting from a lung parenchymal injury and positive pressured ambient air entering a negatively pressured thoracic cavity during inspiration may result in more pressurized air than the conventional 14-gauge catheter is capable of evacuating, given its dimensional limitations. In comparison, the inner cannula 14 of various embodiments of the modified Veress needle 10 has an inner bore diameter of 3.5 mm, which produces a flow rate of 13.1 L/min (assuming a length of 14 cm, a diameter of 3.5 mm, and a pressure gradient of 5 mmHg). This can result in more rapid thoracic decompression and reversal of cardiovascular collapse in patients with tension pneumothorax.

The blind insertion and lack of tactile or visual feedback of the conventional 14-gauge thoracostomy needle are potential sources of complications. Multiple case reports document injuries to the lung, great vessels, and heart from inadvertent needle puncture during tension pneumothorax decompression. The conventional 14-gauge thoracostomy needle has no safety mechanism other than the operator's own discretion on the depth of insertion.

The spring loaded mechanism of the modified Veress needle 10 allows for immediate protection from the sharp bevel 16 of the outer cannula 12 once the needle 10 has entered into the thoracic cavity. In-situ observation of the modified Veress needle 10 during our study noted no injuries to the viscera, despite several instances in which the modified Veress needle 10 was in direct contact with the lung or heart. Furthermore, the protrusion of the proximal end portion 28 of the inner cannula 14 from the housing 22 when the inner cannula 14 is in the retracted position assists the operator in determining the appropriate depth of insertion.

Another design flaw described in several studies involves the composition of the conventional 14-gauge needle thoracostomy catheter. Currently, field tension pneumothorax is most commonly decompressed using a 14 gauge angiocatheter, followed by removal of the needle, leaving only the soft plastic sheath in the wound to minimize unintentional injuries to underlying viscera. It has been repeatedly observed in clinical practice that the conventional catheter easily kinks, which renders it useless for its intended purpose. The modified Veress needle 10 does not utilize a sheathing catheter.

The modified Veress needle 10 effectively overcomes all five problematic areas encountered by the conventional 14-gauge needle thoracostomy. In addition, the modified Veress needle provides both tactile and visual safety features that can render the needle 10 more effective and safer. The technique for placing the modified Veress needle 10 is rapid and relatively easy, making the needle 10 a valuable tool for pre-hospital personnel.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A needle assembly, comprising:
an outer cannula defining a lumen and having a proximal end portion and a distal end portion, the distal end portion comprising a sharp bevel facilitating insertion of the needle assembly into a subject;
an inner cannula slidably disposed coaxially in the lumen of the outer cannula and being movable relative to the outer cannula between an extended position and a retracted position, the inner cannula defining a respective lumen and having a blunt distal end portion and a proximal portion, the blunt distal end portion extending beyond the sharp bevel of the outer cannula whenever the inner cannula is in the extended position and being at least partially retracted within the lumen of the outer cannula whenever the inner cannula is in the retracted position;
a bias coupled to the inner cannula in a manner favoring automatic positioning of the inner cannula at the extended position unless the blunt distal end portion is experiencing a sufficient force to move the inner cannula automatically to the retracted position;
a visual indicator indicating to the user a disposition of the inner cannula relative to the retracted and extended positions;
a housing coupled to the proximal end portion of the outer cannula, the housing being configured to allow the inner cannula to move, coaxially in the outer cannula, relative to the housing, at least a portion of the housing being transparent such that the visual indicator is visible to the user at least whenever the inner cannula is in the retracted position; and
a pierce-depth limiter comprising a flange situated around the outer cannula, the flange being separate and spaced apart from the housing along the outer cannula, the flange being configured to contact an exterior of a body cavity whenever the needle assembly has penetrated to a correspondingly desired depth in the body cavity;
wherein the blunt distal end portion of the inner cannula defines an opening in a side of the inner cannula, the opening being in communication with the lumen of the inner cannula; and wherein the blunt distal end portion further comprises a curved interior surface extending across a diameter of the inner cannula to a distal edge of the opening such that the curved interior surface defines a distal terminus of the lumen of the inner cannula at the opening on the side of the inner cannula.

2. The needle assembly of claim 1, wherein the visual indicator comprises a feature on the proximal portion of the inner cannula that moves with the inner cannula relative to the proximal end portion of the outer cannula.

3. The needle assembly of claim 1, wherein:
the bias is contained in the housing; and
the housing is further configured to allow access to the lumen of the inner cannula through an opening defined in the housing.

4. The needle assembly of claim 1, wherein the housing defines a proximal opening through which the proximal end of the inner cannula extends outwardly from the housing whenever the inner cannula is in the retracted position to indicate that the sharp bevel of the outer cannula is exposed.

5. The needle assembly of claim 1, wherein the bias comprises a compression spring that is coupled to the inner cannula such that the spring is in a less-compressed state when the inner cannula is in the extended position and in a more-compressed state when the inner cannula is in the retracted position.

6. The needle assembly of claim 1, wherein the visual indicator comprises a visually distinguishable feature on the proximal end of the inner cannula that moves, with corresponding coaxial motion of the inner cannula, relative to the outer cannula.

7. The needle assembly of claim 1, wherein:
the bias comprises a compression spring coupled to the inner cannula such that the spring is in a less-compressed state when the inner cannula is in the extended position and in a more-compressed state when the inner cannula is in the retracted position;
the inner cannula is coupled to the compression spring by a spring retainer; and
the visual indicator further comprises a visually distinguishable feature situated on the spring retainer.

8. The needle assembly of claim 7, wherein the spring retainer is coupled to the inner cannula and configured to move with the inner cannula inside the lumen of the outer cannula.

9. The needle assembly of claim 8, wherein the spring retainer is hidden from view in the lumen of the outer cannula whenever the inner cannula is in the extended position.

10. The needle assembly of claim 1, wherein:
the inner cannula has a length;
the lumen of the inner cannula extends the length of the inner cannula to the opening in the blunt distal end portion; and
the lumen defines a route through which one or more implements can be routed to and/or from a body cavity of a subject whenever the needle assembly has been applied to the subject.

11. A method for treating tension pneumothorax in a living subject, comprising:
advancing a Veress-type needle assembly into a thoracic cavity of the subject such that an inner cannula of the needle assembly moves from an extended position to a retracted position coaxially through a lumen of an outer cannula, the needle assembly including a bias coupled to the inner cannula in a manner favoring automatic positioning of the inner cannula in the extended position unless a blunt distal end portion of the inner cannula experiences a sufficient force to move the inner cannula automatically to the retracted position, the outer cannula including a proximal end portion and a distal end portion, the distal end portion comprising a sharp bevel which is exposed when the inner cannula is in the retracted position, wherein a proximal portion of the inner cannula includes a visual indicator to indicate to a user a disposition of the inner cannula relative to the retracted and extended positions, wherein the blunt distal end portion of the inner cannula extends beyond the sharp bevel of the outer cannula whenever the inner cannula is in the extended position and is at least partially retracted within the lumen of the outer cannula whenever the inner cannula is in the retracted position, the blunt distal end portion of the inner cannula defining an opening in a side of the inner cannula, the opening being in communication with the lumen of the inner cannula, the blunt distal end portion further comprising a curved interior surface extending across a diameter of the inner cannula to a distal edge of the opening such that the curved interior surface defines a distal terminus of the lumen of the inner cannula at the opening on the side of the inner cannula; the needle assembly further comprising a housing coupled to the proximal end portion of the outer cannula, the housing being configured to allow the inner cannula to move, coaxially in the outer cannula, relative to the housing, at least a portion of the housing being transparent such that the visual indicator is visible to the user at least whenever the inner cannula is in the retracted position, the needle assembly further comprising a pierce-depth limiter comprising a flange situated around the outer cannula, the flange being separate and spaced apart from the housing along the outer cannula, the flange being configured to contact an exterior of a body cavity whenever the needle assembly has penetrated to a correspondingly desired depth in the body cavity;

halting advancement of the needle assembly into the thoracic cavity when the inner cannula moves from the retracted position to the extended position; and withdrawing fluid from the thoracic cavity through the opening defined in the blunt distal end portion and through the lumen of the inner cannula.

12. The method of claim 11, wherein advancing further comprises piercing the tissue of the thoracic cavity using the sharp bevel of the outer cannula.

13. The method of claim 11, further comprising alertng a user by changing a visual aspect of the proximal end portion of the inner cannula when the sharp bevel of the outer cannula is exposed.

14. The method of claim 11, further comprising: inserting a guide wire into the thoracic cavity through the lumen of the inner cannula such that the guide wire is urged outwardly through the opening by the curved interior surface; and withdrawing the needle assembly from the thoracic cavity, as guided by the guide wire, while leaving the guide wire extending into the thoracic cavity.

15. The method of claim 14, further comprising: passing a catheter along the guide wire into the thoracic cavity such that a distal end ofthe catheter is located within the thoracic cavity; and passing a fluid from the thoracic cavity through the catheter.

16. The method of claim 15, wherein the catheter is a pigtail catheter.

17. The method of claim 11, further comprising displaying the visual indicator to a user indicating that the sharp bevel of the outer cannula is exposed.

18. The method of claim 17, further comprising displaying the visual indicator through the housing of the needle assembly.

19. The method of claim 11, wherein during the inserting step the inner cannula moves from the retracted position to the extended position after the thoracic cavity is pierced such that the blunt distal end portion of the inner cannula extends past the sharp bevel of the outer cannula.

20. The needle assembly of claim 1, wherein the sharp bevel of the outer cannula comprises a radiused surface having a concavity that curves radially outward away from an outer surface of the inner cannula.

21. The needle assembly of claim 1, wherein:
the blunt distal end portion comprises a dome-shaped distal portion and a proximal portion received in the inner cannula; and
the curved interior surface is formed in the proximal portion of the blunt distal end portion.

22. The needle assembly of claim 1, wherein an exterior surface of the housing is configured to be gripped by a user.

* * * * *